(12) United States Patent
Lauf et al.

(10) Patent No.: US 11,134,936 B2
(45) Date of Patent: Oct. 5, 2021

(54) ORTHOPEDIC RETRACTOR FOR LATERAL SPINE SURGERY

(71) Applicant: Life Spine, Inc., Huntley, IL (US)

(72) Inventors: Garrett D. Lauf, Hampshire, IL (US); Daniel P. Predick, West Lafayette, IN (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 16/351,298

(22) Filed: Mar. 12, 2019

(65) Prior Publication Data
US 2019/0274671 A1    Sep. 12, 2019

Related U.S. Application Data

(60) Provisional application No. 62/641,782, filed on Mar. 12, 2018.

(51) Int. Cl.
*A61B 17/02* (2006.01)
*A61F 2/46* (2006.01)

(52) U.S. Cl.
CPC ........ *A61B 17/0206* (2013.01); *A61B 17/025* (2013.01); *A61B 17/0218* (2013.01); *A61B 2017/0256* (2013.01); *A61F 2/4611* (2013.01)

(58) Field of Classification Search
CPC ............ A61B 17/0206; A61B 17/0218; A61B 17/025; A61B 2017/0256; A61B 2/4611; A61B 1/32; A61B 17/02–201/0275
See application file for complete search history.

(56) References Cited

U.S. PATENT DOCUMENTS

| | | | |
|---|---|---|---|
| 7,931,589 B2* | 4/2011 | Cohen | A61B 17/0206 600/210 |
| 8,313,430 B1* | 11/2012 | Pimenta | A61B 17/0206 600/202 |
| 8,353,826 B2* | 1/2013 | Weiman | A61B 17/0206 600/219 |

(Continued)

FOREIGN PATENT DOCUMENTS

| | | | |
|---|---|---|---|
| WO | 2012/040206 A1 | 3/2012 | |
| WO | 2015/134367 A1 | 9/2015 | |
| WO | WO-2016040497 A1 * | 3/2016 | ........... A61B 5/4893 |

*Primary Examiner* — Zade Coley
(74) *Attorney, Agent, or Firm* — Foley & Lardner LLP

(57) ABSTRACT

A spine retractor provides lateral access to the spine for distracting soft tissue and psoas muscle for spinal fusion procedures utilizing position controllable blades. The retractor allows concerted linear distraction of two lateral blades and separate linear distraction of one medial blade. Individual angulation assemblies associated with each blade provides separately controllable angulation. Handles attached to the two lateral blades control their distraction while a medial knob controls medial blade distraction. An expansion knob associated with each handle provides individually precise distraction of its associated blade. Each angulation assembly comprises an angulation knob that threads into a distal arm of a blade holder assembly and is received into a spherical ball seated in a spherical pocket in a mating proximal arm of the blade holder assembly. Torque applied to the spherical ball by the angulation knob causes distal arm angulation relative to the proximal. Each distal arm holds a blade assembly having a blade.

15 Claims, 13 Drawing Sheets

(56) References Cited

U.S. PATENT DOCUMENTS

| | | | |
|---|---|---|---|
| 9,381,008 B2* | 7/2016 | Thornburg | A61B 17/0206 |
| 9,408,598 B1* | 8/2016 | Fantini | A61B 6/0492 |
| 9,693,762 B2* | 7/2017 | Reimels | A61B 17/0206 |
| 2012/0245431 A1* | 9/2012 | Baudouin | A61B 17/0293 |
| | | | 600/213 |
| 2015/0250466 A1 | 9/2015 | Thornburg | |
| 2016/0051242 A1* | 2/2016 | Predick | A61B 17/0206 |
| | | | 600/224 |
| 2016/0317137 A1* | 11/2016 | Predick | A61B 17/0206 |

\* cited by examiner

ORTHOPEDIC RETRACTOR FOR LATERAL SPINE SURGERY

CROSS-REFERENCE TO RELATED APPLICATIONS

This U.S. non-provisional patent application claims the benefit of and/or priority under 35 U.S.C. § 119(e) to U.S. provisional patent application Ser. No. 62/641,782 filed Mar. 12, 2018 titled "Lateral Spine Retractor" the entire contents of which is specifically incorporated herein by reference.

FIELD OF THE INVENTION

The present invention relates to retractors used in orthopedic surgery and, more particularly, to retractors used for lateral spine surgery.

BACKGROUND OF THE INVENTION

Many surgical procedures necessitate the use of a medical device known as a surgical retractor. A surgical retractor is used to separate the edges of a surgical incision or wound, or to hold back underlying organs and tissues so that body parts under the incision may be accessed. A wide variety of retractors are used for various types of surgical procedures such as orthopedic surgery, cosmetic surgery, cardiothoracic surgery, gastrointestinal surgery, gynecological surgery, urological surgery, and others. Surgical retractors are thus uniquely designed for different functions.

Within the category of orthopedic surgery there are various types of retractors depending on whether the procedure involves the leg, hip, arm, shoulder, or spine. There are even variations in retractors within the category of orthopedic spine surgery depending on whether the procedure involves the lumbar, cervical, thoracic, or sacrum portion of the spine. Orthopedic retractors for the spine are even further differentiated by whether the spine surgery is an anterior approach or procedure, a posterior approach or procedure, or a lateral approach or procedure.

One type of spine surgery that utilizes a lateral approach or procedure is vertebral fusion. In vertebral fusion the vertebral disc between adjacent vertebrae is removed or supplemented with an implant known as a cage or interbody device. A retractor is used to hold the incision and/or the adjacent vertebrae in order to remove the disc and/or install the implant. It may also be used for other purposes during the spinal procedure.

Orthopedic retractors for spine surgery typically use blades that can be manipulated in order to perform various functions. It is thus desirable for the blades of the orthopedic retractor to be easily manipulated by the surgeon. It is also desirable that the retractor allow the blades to be moved in various directions and/or placed in various positions. It is also desirable that the retractor allow the blades to be manipulated into particular orientations. Prior art orthopedic retractors for lateral spine surgery are currently deficient in these abilities.

It is therefore an object of the present invention to provide an orthopedic retractor for lateral spine surgery that overcomes the deficiencies of the prior art. It is also an object of the present invention to provide an orthopedic retractor that incorporates one or more of the above desires.

The aforementioned and other objects and desires are satisfied by the present orthopedic retractor for lateral spine surgery.

SUMMARY OF THE INVENTION

An orthopedic retractor provides lateral access to the lumbar portion of the spine utilizing a minimally invasive technique by distracting (drawing apart) soft tissue and psoas muscle leading up to the lumbar disc for a spinal fusion procedure by position controllable blades. The orthopedic retractor provides linear distraction of its blades as well as blade angulation in order to minimize the amount of tissue disruption and maximize exposure of the lumbar disc space.

The orthopedic retractor has two lateral blades and one medial blade. Each lateral blade is attached to a lateral blade arm/arm assembly that is attached to a handle for controlling distraction. The medial blade is attached to a medial arm/arm assembly that is attached to a medial drive assembly for controlling its distraction. The medial drive assembly has a threaded rod that is attached at one end to the medial arm assembly and at another end to a medial knob wherein rotation thereof controls distraction of the medial blade. Opening and closing of the handles draws apart (distracts) and draws close (retracts) the lateral blades. Rotation of the medial knob in one direction distracts the medial blade while rotation of the middle knob in an opposite direction retracts the medial blade.

Proximal portions of the handles may be detached for easier access to the medial knob.

A distraction control assembly is associated with each handle and provides precise and individual adjustment of handle position for precise and individual distraction and retraction of the lateral blade associated with the particular handle. Each distraction control assembly includes a spring loaded threaded expansion knob extending through the handle and threadedly received in the body.

Angulation assemblies are associated with each of the two lateral arm assemblies and the medial arm assembly, and are used to individually angulate the lateral blades and the medial blade for maximum exposure. The angulation assemblies provide individual control of the angle or tilt of each blade.

In one form, each angulation assembly consists of a threaded angulation knob that threads into a distal arm of a blade holder assembly and a spherical ball that is seated in a spherical pocket in a mating proximal arm of the blade holder assembly. The threaded angulation knob is received by the spherical ball. When torque is applied to the spherical ball by the threaded angulation knob, it will cause the distal arm to tilt or angulate relative to the proximal arm. Each distal arm holds a blade assembly having a blade.

The blade assembly consists of a blade holder and a blade. The blade holder is configured for reception in an associated distal arm of the blade holder assembly—i.e. a first lateral distal arm for the first lateral blade, a second lateral distal arm for the second lateral blade, and a medial distal arm for the medial blade. The first lateral distal arm is connected to the first lateral proximal arm of the blade holder assembly, the second lateral distal arm is connected to the second lateral proximal arm of the blade holder assembly, and the medial distal arm is connected to the medial proximal arm.

Each blade assembly includes a blade lock that is inserted into the distal arm and threaded into the blade. The blade lock has a landing that sits on top of the arm and retains the blade in the arm house. There is also a c-clip that prevents the blade lock from coming out after the blade is removed.

The orthopedic retractor is preferably, but not necessarily, made from a combination of surgical grade stainless steel, titanium, and plastic.

BRIEF DESCRIPTION OF THE DRAWING FIGURES

The above mentioned and other features and objects of this invention, and the manner of attaining them, will become more apparent and the invention itself will be better understood by reference to the following description of a form of the invention taken in conjunction with the accompanying drawings, wherein.

A detailed description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF THE INVENTION

Figure 25:
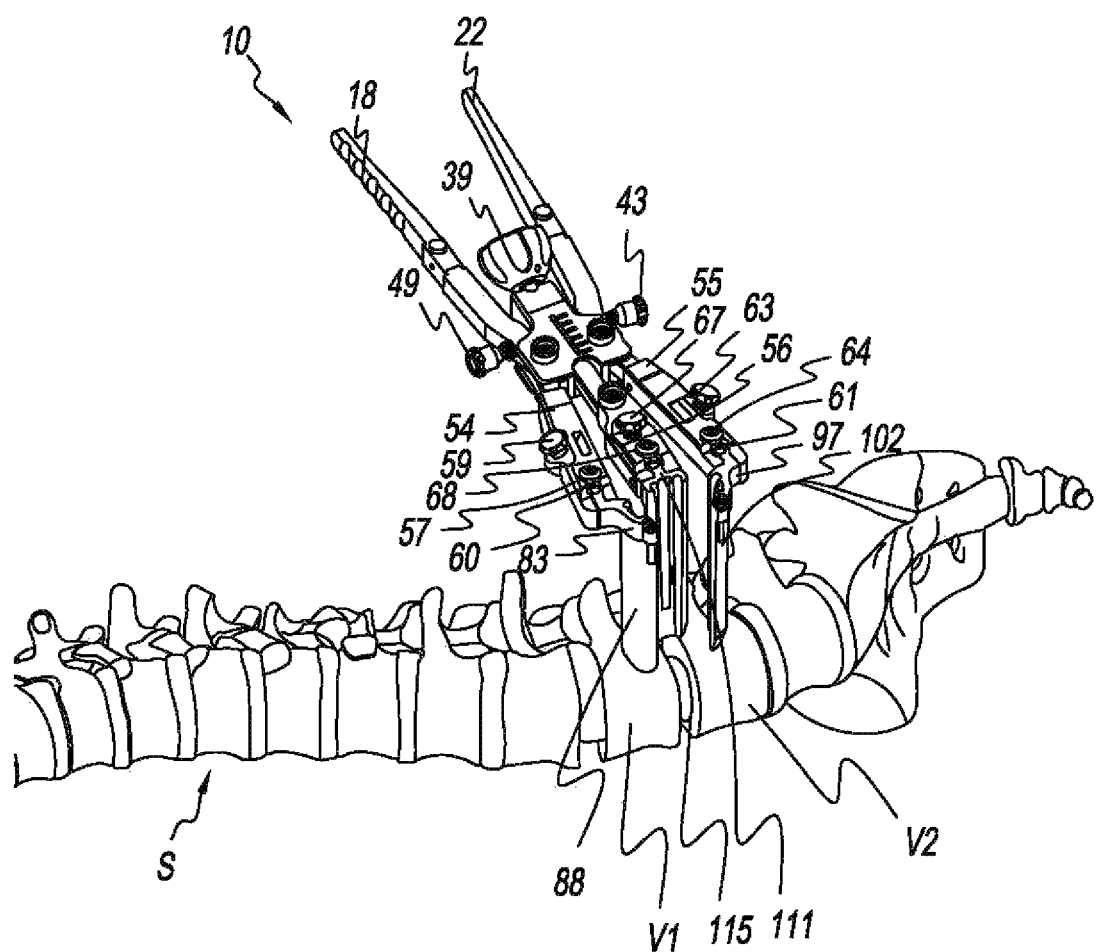
FIG. 25 is an isometric view of the orthopedic retractor of FIG. 1 ready to perform a lateral spine procedure on the lumbar portion of the spine.

FIGS. 1-24 depict various views of an orthopedic retractor, generally designated 10, and/or its constituent components fashioned in accordance with the present principles, for use in lateral spine surgery/surgical procedures as exemplified in the illustration of FIG. 25, and with and without retractor blades, distracted or not distracted, and with some of the retractor blades angulated. Reference is thus made to the Description of the Drawing Figures. The orthopedic retractor, spine retractor, or lateral spine retractor 10 is preferably, but not necessarily, fashioned from various surgical grade materials such as stainless steel, titanium, and plastic, the plastic preferably, but not necessarily, being a polyphenylsulfone (PPSU), a sulfone polymer. Such a PPSU may be Radel® made by Aetna Plastics Corp of Valley View Ohio, U.S. Other surgical grade materials may be used. The lateral retractor 10 is used to provide lateral access to the spine and preferably, but not necessarily, the lumbar portion of the spine as illustrated in FIG. 25. The orthopedic retractor 10 is preferably, but not necessarily, used for a minimally invasive technique by distracting the soft tissue and psoas muscle leading up to the lumbar disc for spinal fusion. The retractor allows for linear distraction as well as blade angulation to minimize the amount of tissue disruption and for maximum exposure to the lumbar disc space. Other spinal surgical procedures are contemplated. It should be appreciated that the nomenclature first and second used herein is arbitrary, as is upper and lower, unless specifically indicated otherwise.

As best seen in FIGS. 3-6, the orthopedic retractor 10 has a generally rectangular body 12 defining a box-like neck 26 with a first upper flange 27 formed generally on a first lateral side, a first lower flange 28 formed generally on the first lateral side but axially below the first upper flange 27, a second upper flange 32 formed generally on a second lateral side opposite the first lateral side, and a second lower flange 33 formed generally on the second lateral side but axially below the second upper flange 28. A cavity 29 is defined between the first upper flange 27 and the first lower flange 28. A post 30 is disposed at a distal end of the cavity 29 between the lower surface of the first upper flange 27 and the upper surface of the first lower flange 28. The cavity 29 receives a distal or lower portion 23 of a second handle 15 while the post 30 pivotally retains the distal portion 23 of the second handle 15. A cavity 34 is defined between the second upper flange 32 and the second lower flange 33. A post 35 is disposed at the distal end of the cavity 34 between the lower surface of the second upper flange 32 and the upper surface of the second lower flange 33. The cavity 34 receives a distal or lower portion 19 of a first handle 14 while the post 35 pivotally retains the distal portion 19 of the first handle 14.

Figure 1:
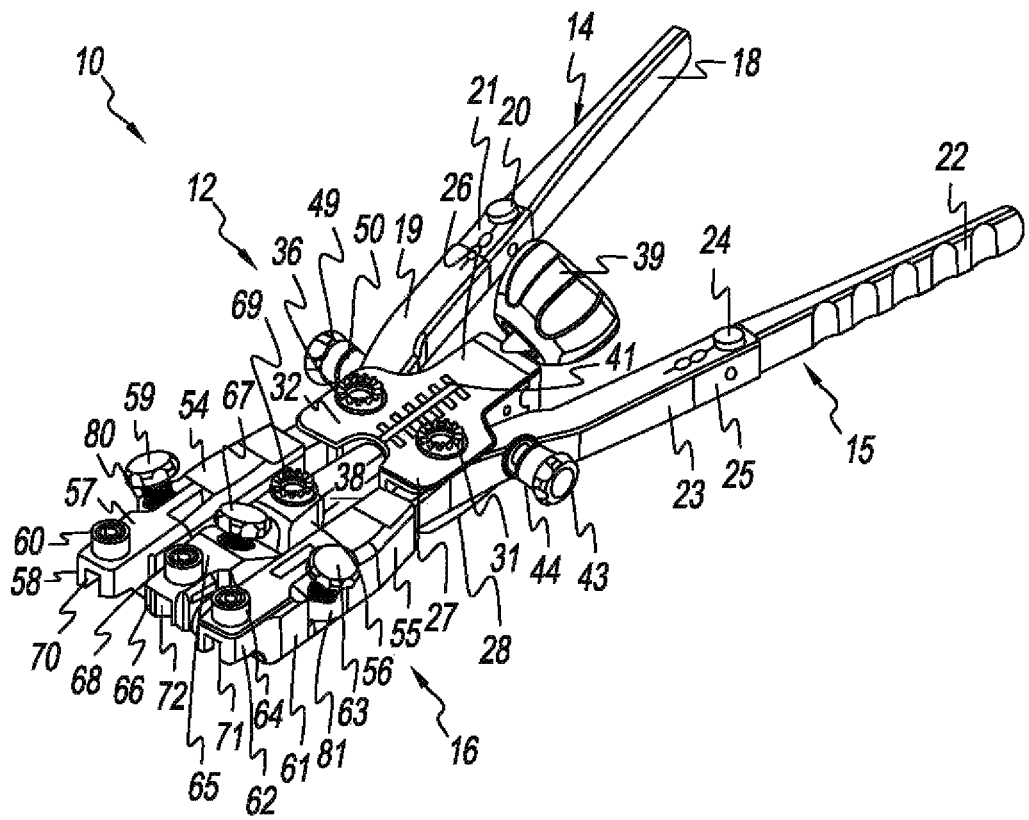
FIG. 1 is an isometric upper view of an orthopedic retractor for lateral spine surgery fashioned in accordance with the present principles, the orthopedic retractor shown without retractor blades and in a non-distracted state.
Figure 2:
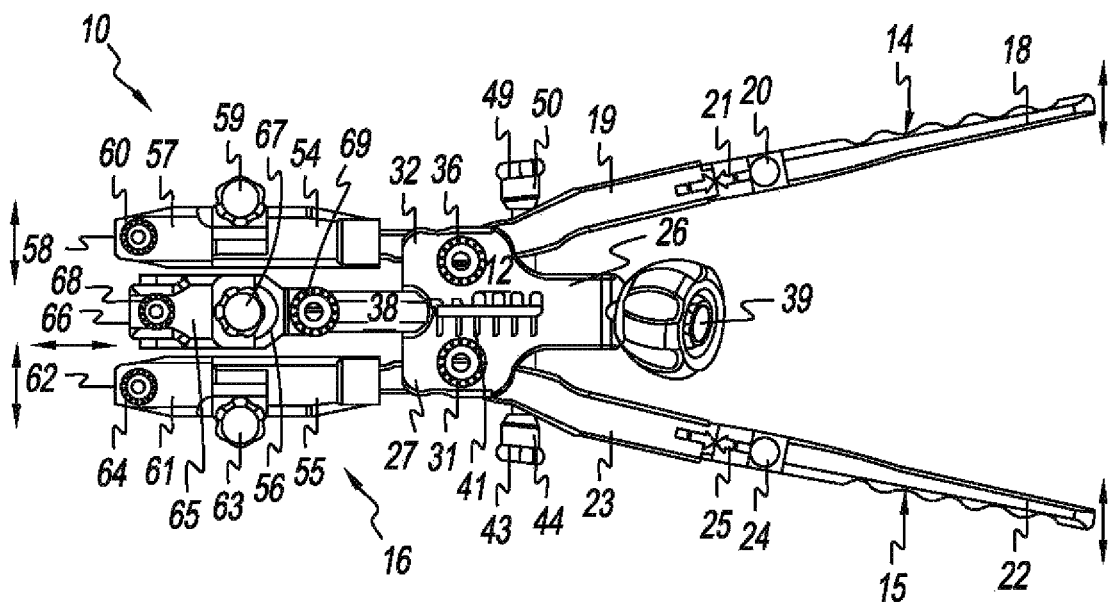
FIG. 2 is a top plan view of the orthopedic retractor of FIG. 1 without retractor blades and in a non-distracted state.
Figure 3:
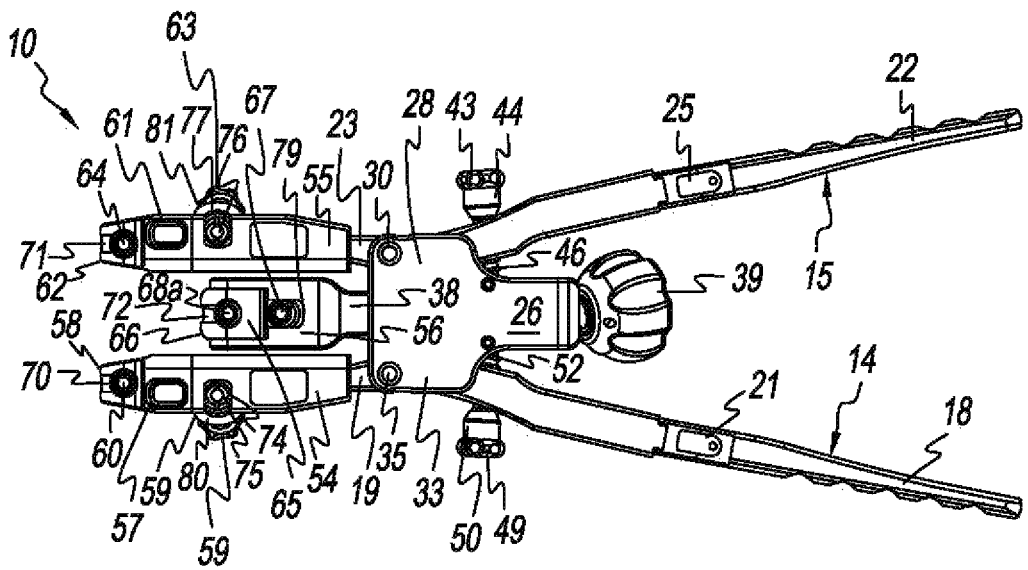
FIG. 3 is a bottom plan view a bottom plan view of the orthopedic retractor of FIG. 1 without retractor blades and in a non-distracted state.
Figure 4:
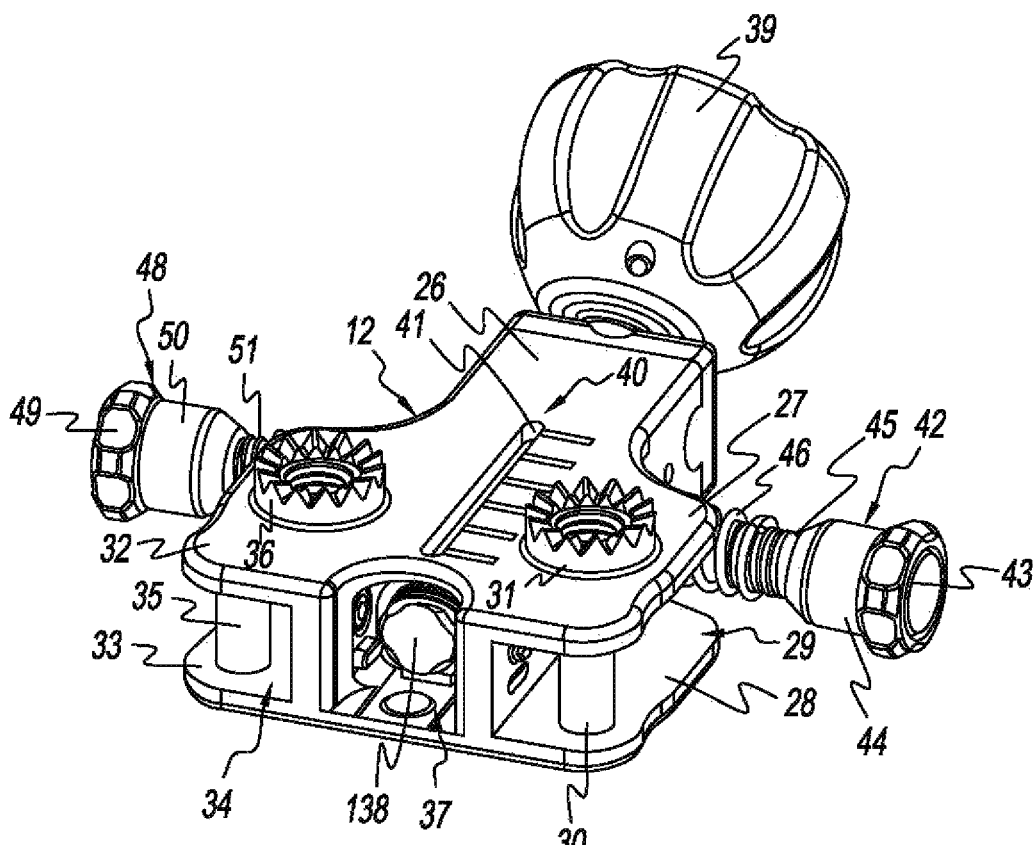
FIG. 4 is an enlarged isometric upper view of a body of the orthopedic retractor of FIG. 1 without its blade holder assembly or handles.
Figure 5:
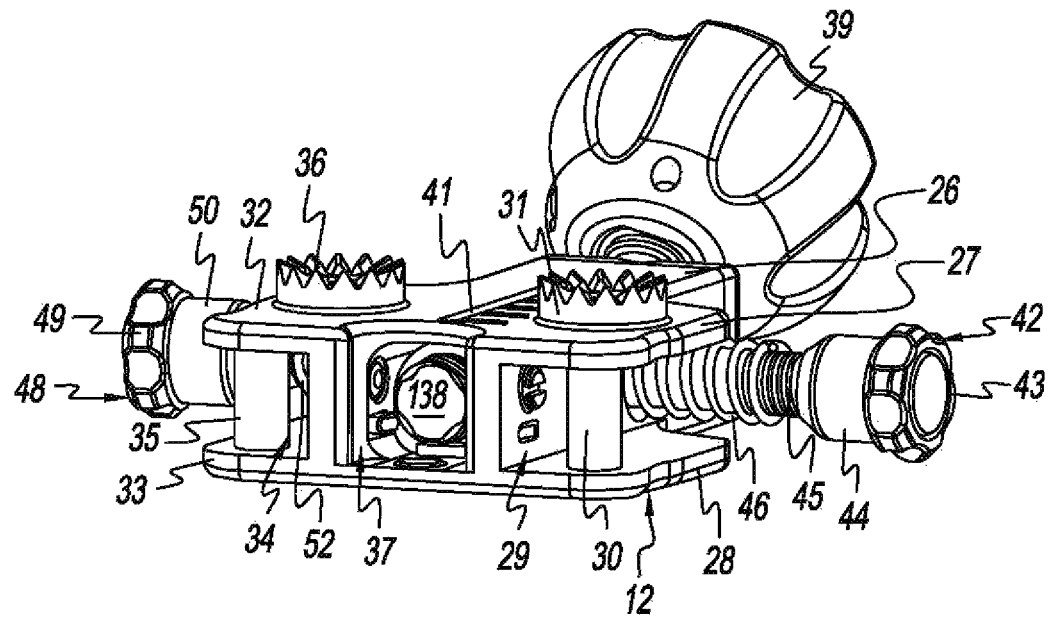
FIG. 5 is another enlarged isometric upper view of the body of FIG. 4 without its blade holder assembly or handles.
Figure 6:
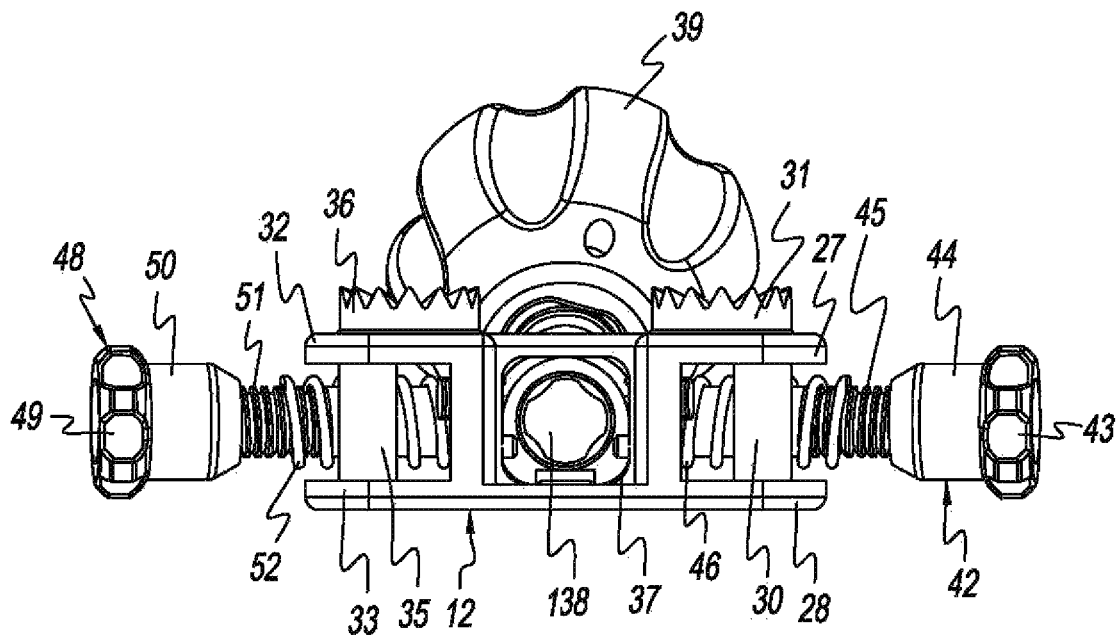
FIG. 6 is an enlarged front view of the body of FIG. 4 without its blade holder assembly or handles.

As best seen in FIGS. 1-3, the first handle 14 is formed by a proximal or upper handle portion 18 and a distal or lower handle portion 19. The upper handle portion 18 is detachably joined to the lower handle portion 19 by a connector or attachment mechanism 21. A button 20 or the like allows release of the upper handle portion from the lower handle portion via the connector/attachment mechanism 21. The lower handle portion 19 is pivotally coupled to the body 12 via the pivot post 30. The lower handle portion 19 has a distal end that is curved outwardly relative to a proximal end thereof and to the upper handle portion 18. Inward movement of the upper handle portion 18 pivots the lower handle portion 18 outward (distraction). Outward movement of the upper handle portion 18 pivots the lower handle portion 18 inward (retraction). Overall, inward movement of the first handle 14 produces distraction while outward movement of the first handle 14 produces retraction. As developed more fully below, the lower handle portion 19 is connected to a first lateral arm assembly consisting of a first lateral proximal or upper arm 54 and a first lateral distal or lower arm 57 of a blade holder assembly 16 which holds a first lateral blade 88. The first handle 14 thus provides distraction and retraction of the first lateral blade 88.

The second handle 15 is formed by a proximal or upper handle portion 22 and a distal or lower handle portion 23. The upper handle portion 22 is detachably joined to the lower handle portion 23 by a connector or attachment mechanism 25. A button 24 or the like allows release of the upper handle portion from the lower handle portion via the connector/attachment mechanism 25. The lower handle portion 23 is pivotally coupled to the body 12 via the pivot post 35. The lower handle portion 23 has a distal end that is curved outwardly relative to a proximal end thereof and to the upper handle portion 22. Inward movement of the upper handle portion 22 pivots the lower handle portion 23 outward (distraction). Outward movement of the upper handle portion 22 pivots the lower handle portion 23 inward (retraction). Overall, inward movement of the second handle 15 produces distraction while outward movement of the second handle 15 produces retraction. As developed more fully below, the lower handle portion 23 is connected to a second lateral arm assembly consisting of a second lateral proximal or upper arm 55 and a second lateral distal or lower arm 61 of the blade holder assembly 16 which holds a second lateral blade 102. The second handle 15 thus provides distraction and retraction of the second lateral blade 102.

The body 12 carries a medial drive assembly 37 having a threaded screw 138 that extends from the distal end of the body 12 to the proximal end of the body 12. A medial knob 39 is attached to the proximal end of the threaded screw 138. Rotation of the medial knob 39 rotates the threaded screw 138. The medial knob 39 allows rotation in the clockwise and counter-clockwise directions which rotates the threaded screw 138 in the clockwise and counter-clockwise directions. The medial drive assembly 37 controls distraction of a medial blade 115 as further explained below. A gauge 40 is provided on the body 12 for indicating amount of medial blade distraction. The gauge 40 includes a slot 41 that allows viewing of the threaded screw 138 such that a mark, marker or otherwise on the threaded screw 138 can be seen within the slot 41. Side demarcations are provided on the body adjacent the slot 41. Movement of the threaded screw 138 moves the mark/marker along the side demarcations.

A first serrated nut 31 is disposed on the upper surface of the first upper flange 27 while a second serrated nut 36 is disposed on the upper surface of the second upper flange 32. The serrated nuts 31, 35 are configured for fixation to a table arm (not shown) that is mounted on a table (not shown) that the patient is lying on for the surgical procedure. The table arm can be manipulated into any position and then fixed rigidly so the retractor does not move (except for blade distraction and angulation) during the surgery. A further serrated nut 69 for table arm fixation may be provided on a medial proximal arm 56 of a medial arm assembly comprising the medial proximal arm 56 and a medial distal arm 65.

The body 12 also includes a first distraction control assembly 42 that provides precise distraction and retraction of the first lateral blade 88. The first distraction control assembly 42 provides fine-tuning adjustment of distraction/retraction of the first lateral blade 88. The first distraction control assembly 42 includes a bolt 43 having a neck 44 that narrows to a threaded shaft 45. The threaded shaft 45 extends through a bore in the lower or distal handle portion 19 of the first handle 14 and is threadedly received by the body 12. A spring 46 is provided on the threaded shaft 45 between the lower or distal handle portion 19 and the body 12 to bias the first handle 14 outwardly. Rotation of the bolt 43 in one direction pushes the first handle 14 inwardly for distraction of the first lateral blade 88, while rotation of the bolt 43 in the opposite direction allows the spring 46 to bias the first handle 14 outwardly for retraction of the first lateral blade 88.

The body 12 further includes a second distraction control assembly 48 that provides precise distraction and retraction of the second lateral blade 102. The second distraction control assembly 48 provides fine-tuning adjustment of distraction/retraction of the second lateral blade 102. The second distraction control assembly 48 includes a bolt 49 having a neck 50 that narrows to a threaded shaft 51. The threaded shaft 51 extends through a bore in the lower or distal handle portion 23 of the second handle 15 and is threadedly received by the body 12. A spring 52 is provided on the threaded shaft 51 between the lower or distal handle portion 23 and the body 12 to bias the second handle 15 outwardly. Rotation of the bolt 49 in one direction pushes the second handle 15 inwardly for distraction of the second lateral blade 102, while rotation of the bolt 49 in the opposite direction allows the spring 52 to bias the second handle 15 outwardly for retraction of the second lateral blade 102.

In addition to the first lateral arm assembly consisting of the first lateral proximal or upper arm 54 and the first lateral distal or lower arm 57 which holds the first lateral blade 88, and the second lateral arm assembly consisting of the second lateral proximal or upper arm 55 and the second lateral distal or lower arm 61 which holds the second lateral blade 102, the blade holder assembly 16 has a medial arm assembly consisting of a medial proximal or upper arm 56 and a medial distal or lower arm 65 which hold a medial blade 115. The medial arm assembly provides distraction and retraction of the medial blade 115.

Figure 7:
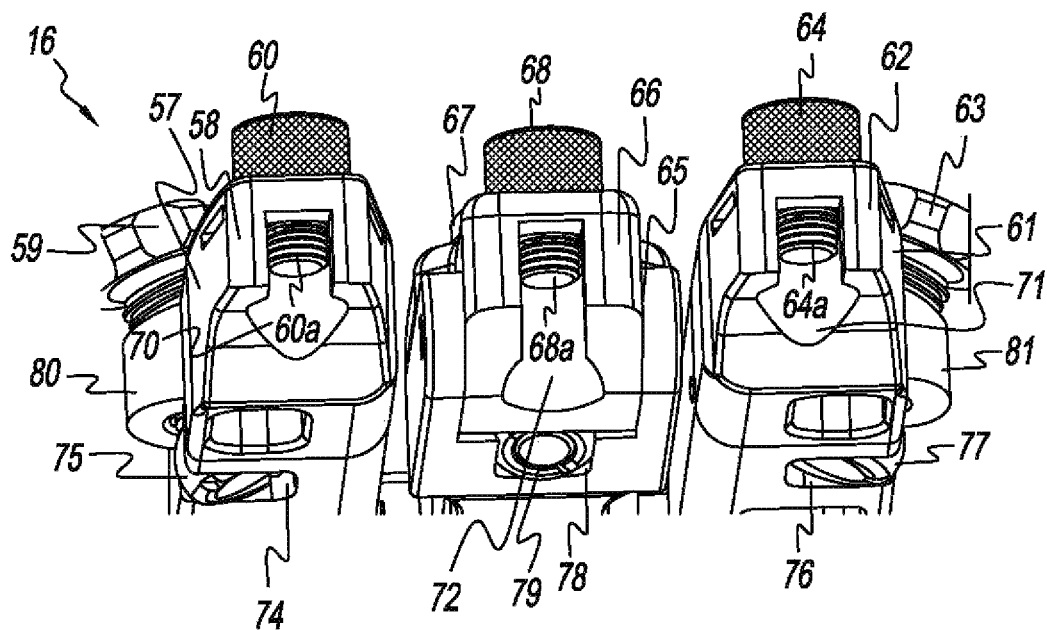
FIG. 7 is an enlarged isometric front view of the distal arms of the blade holder assembly of the orthopedic retractor of FIG. 1 without blades.
Figure 8:
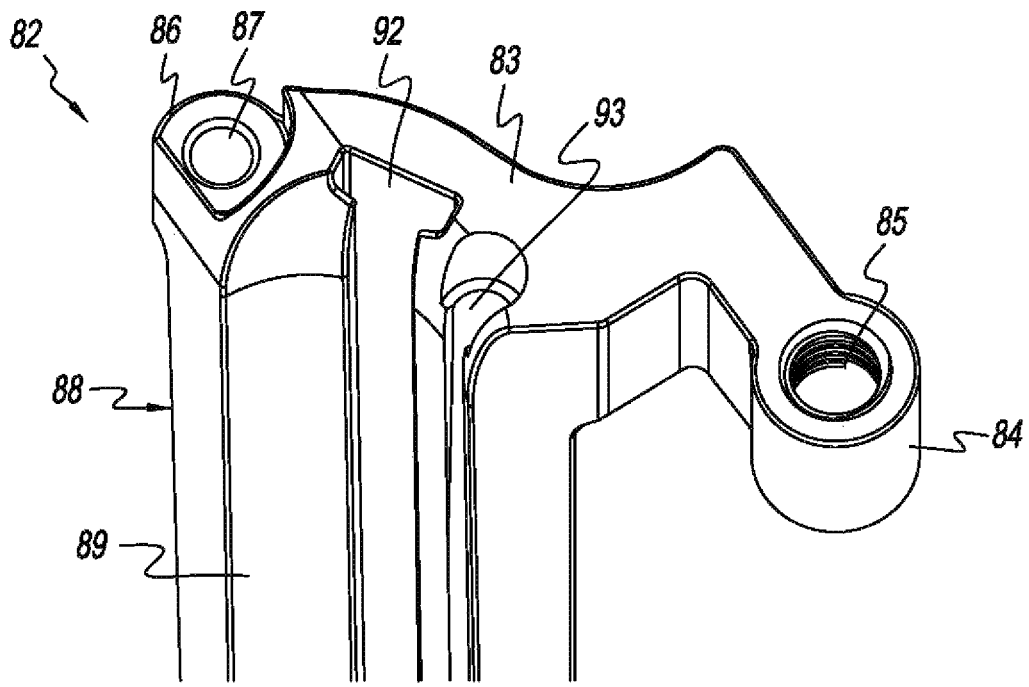
FIG. 8 is an enlarged isometric top view of an upper portion of a blade assembly of the orthopedic retractor of FIG. 1.
Figure 9:
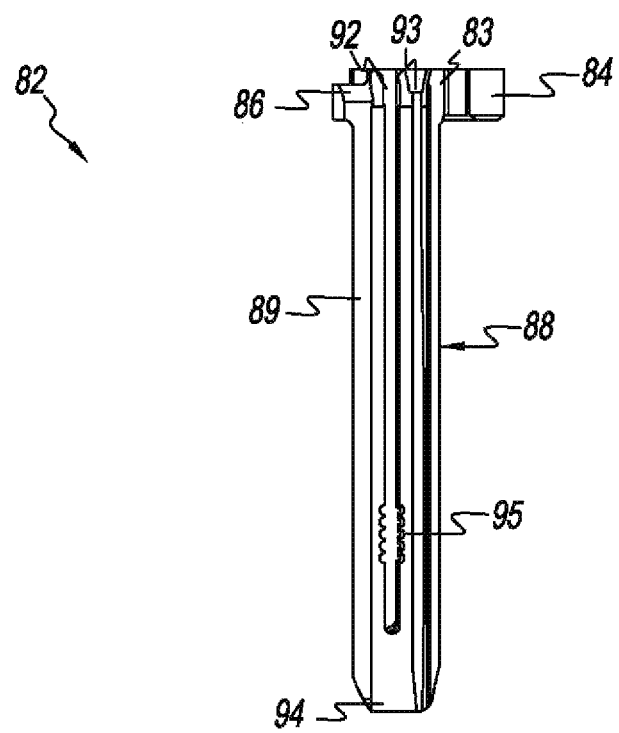
FIG. 9 is a proximal plan view of a blade assembly of the orthopedic retractor of FIG. 1.
Figure 10:
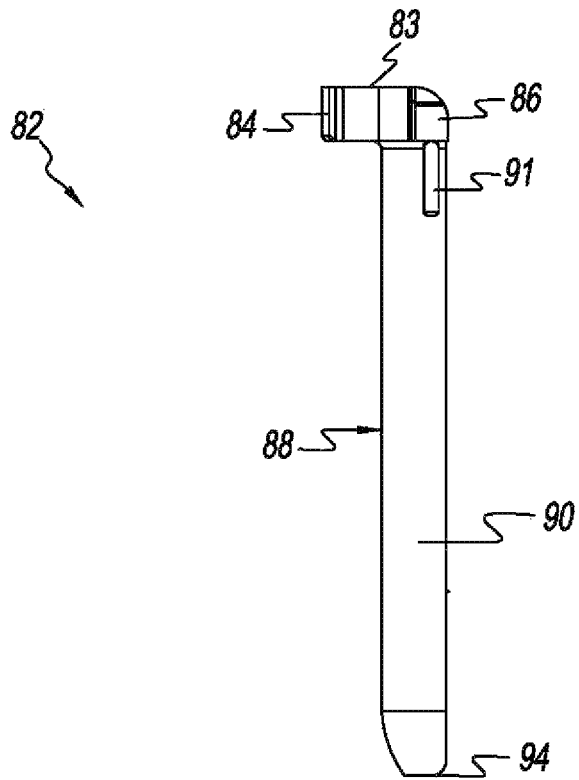
FIG. 10 is a lateral plan view the blade assembly of FIG. 9.
Figure 11:
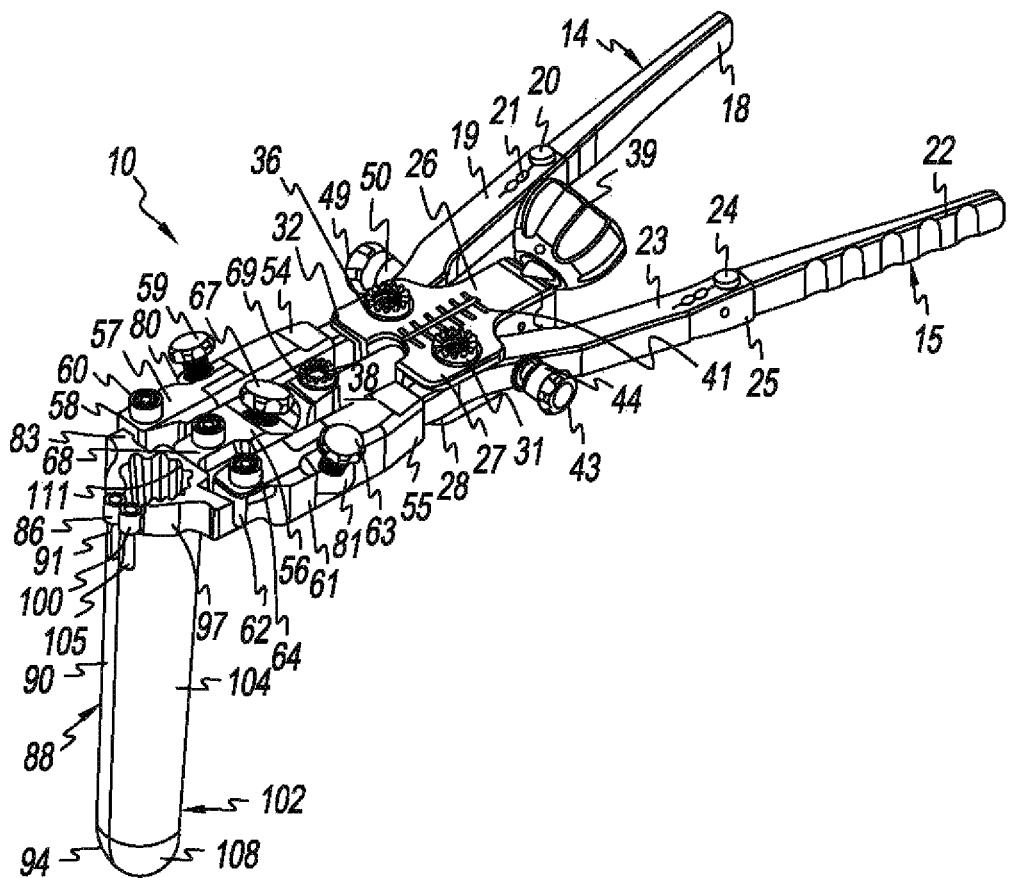
FIG. 11 is an isometric upper view of the orthopedic retractor of FIG. 1 shown with retractor blades and in a non-distracted state.
Figure 12:
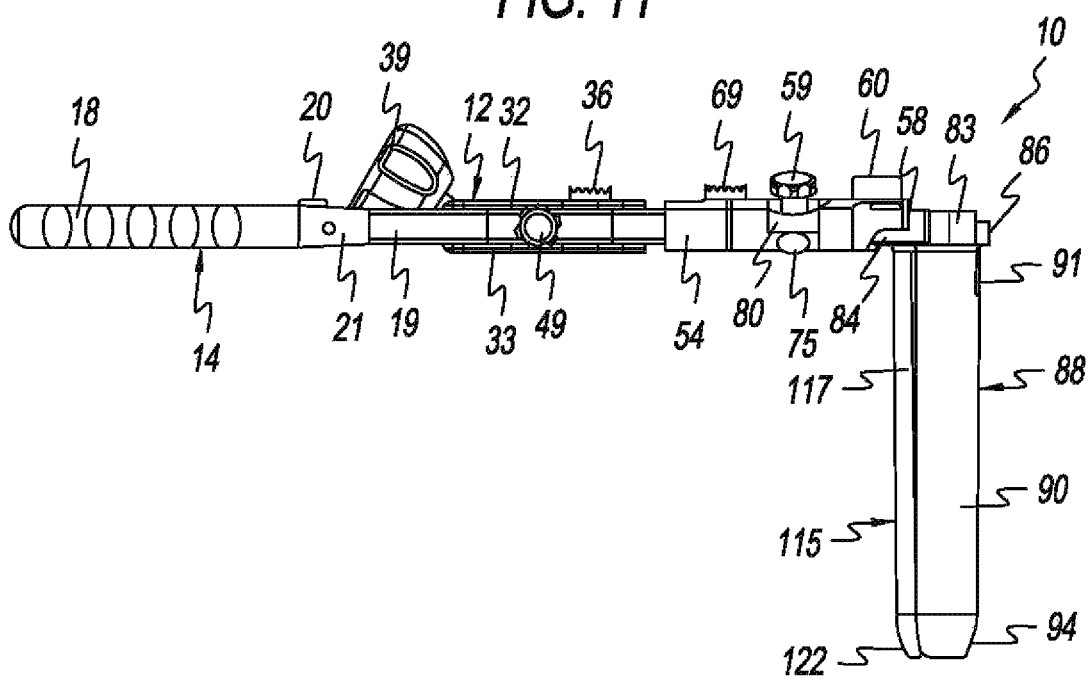
FIG. 12 is a side view of the orthopedic retractor of FIG. 11.
Figure 13:
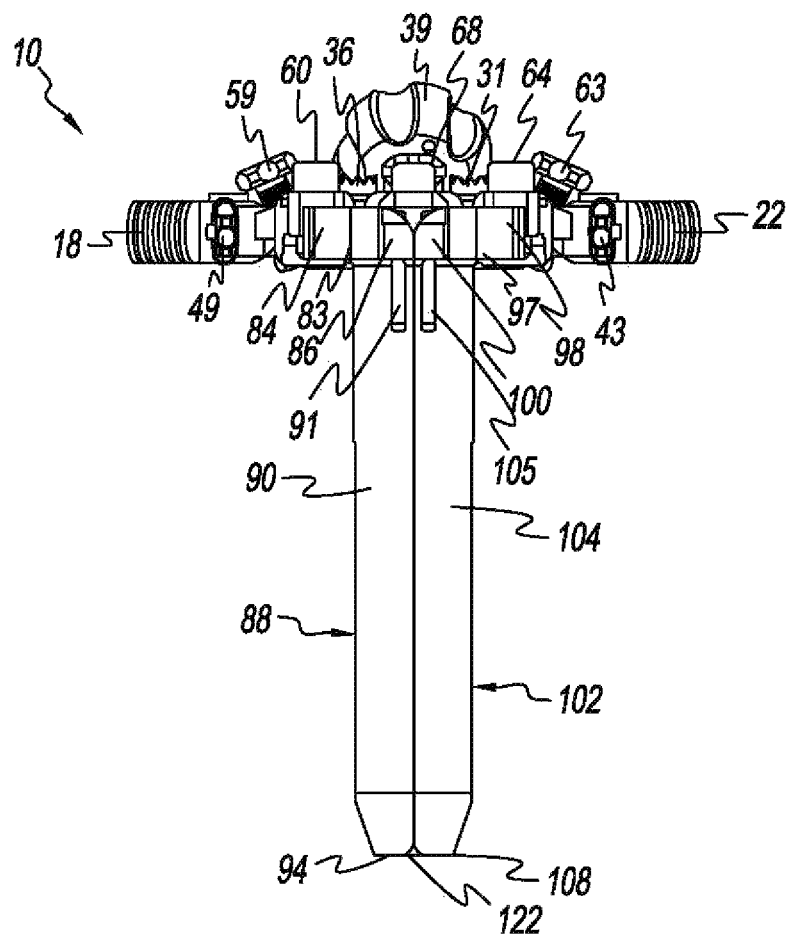
FIG. 13 is a front view of the orthopedic retractor of FIG. 11.
Figure 14:
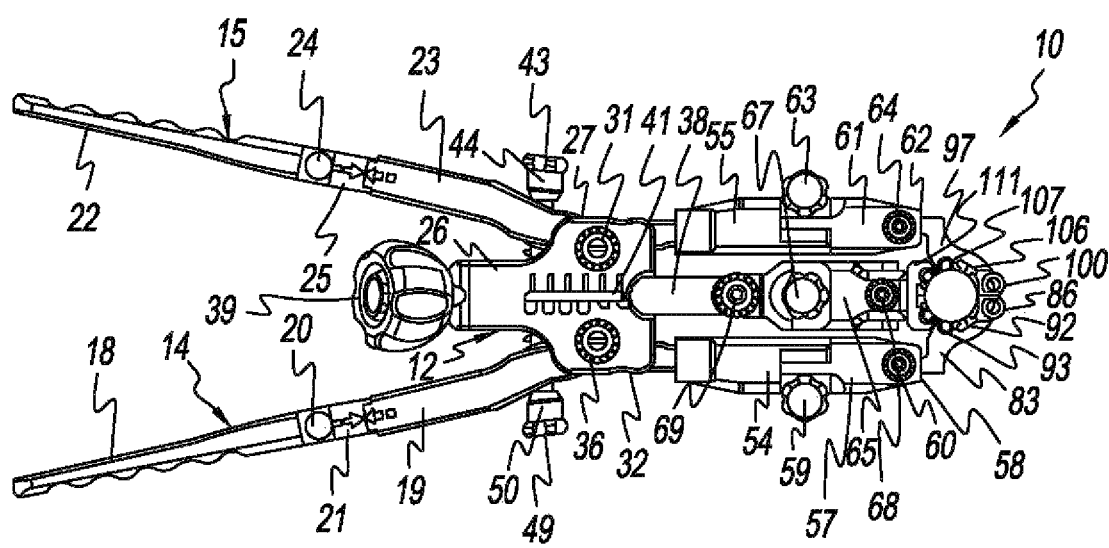
FIG. 14 is a top plan view of the orthopedic retractor of FIG. 1 shown with retractor blades and in a non-distracted state.
Figure 15:
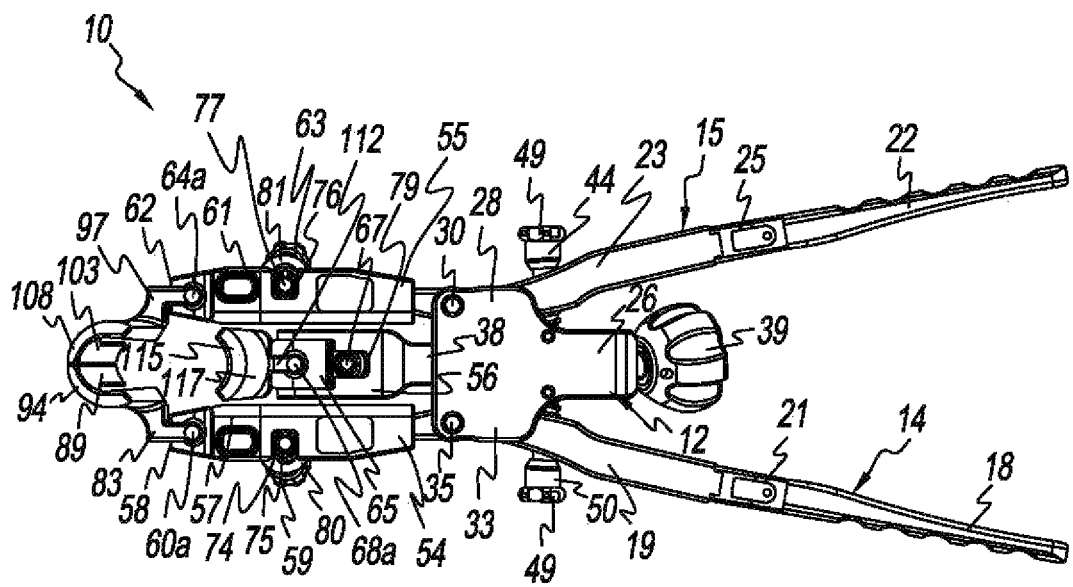
FIG. 15 is a bottom plan view of the orthopedic retractor of FIG. 1 shown with retractor blades and in a non-distracted state.
Figure 16:
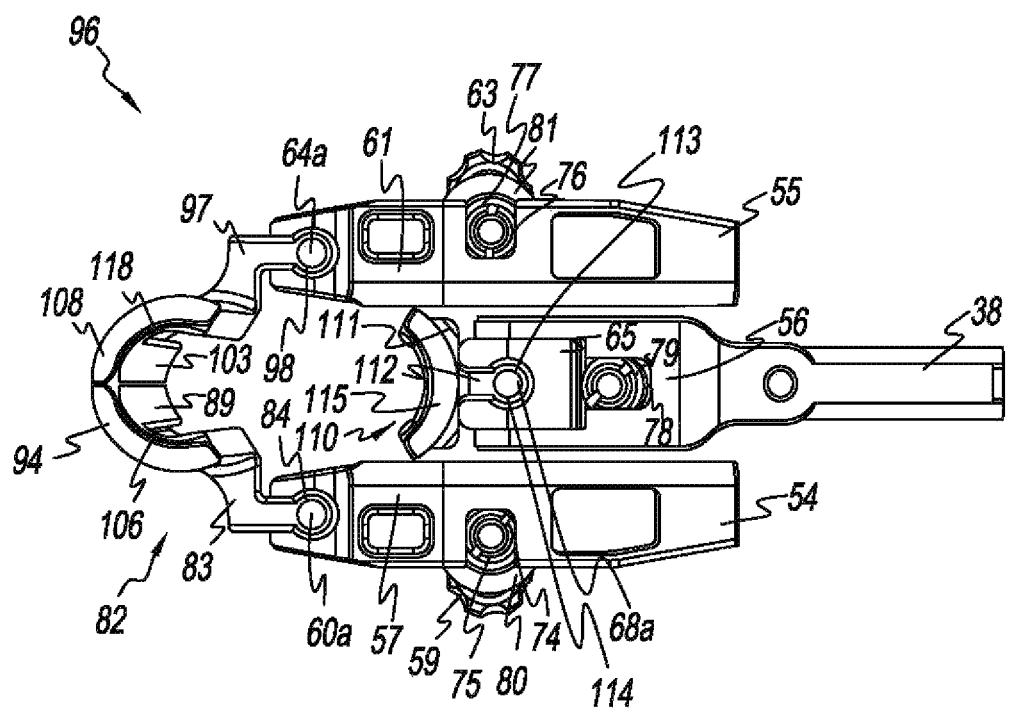
FIG. 16 is an enlarged bottom plan view of the blade holder assembly of the orthopedic retractor of FIG. 1.
Figure 17:
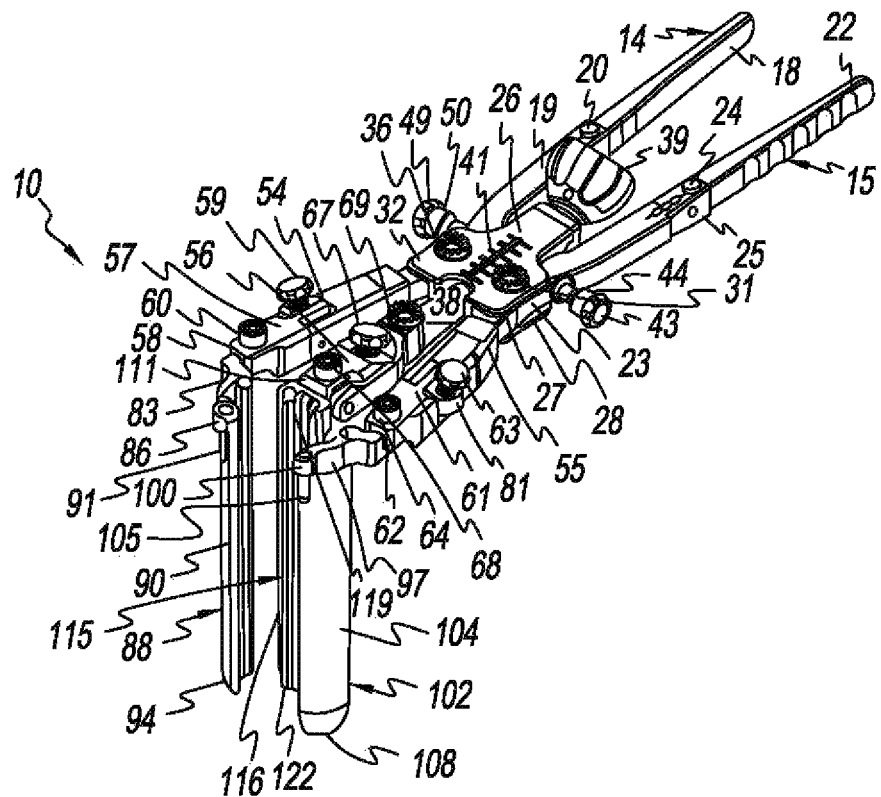
FIG. 17 is an isometric upper view of the orthopedic retractor of FIG. 1 shown with retractor blades and in a distracted state.
Figure 18:
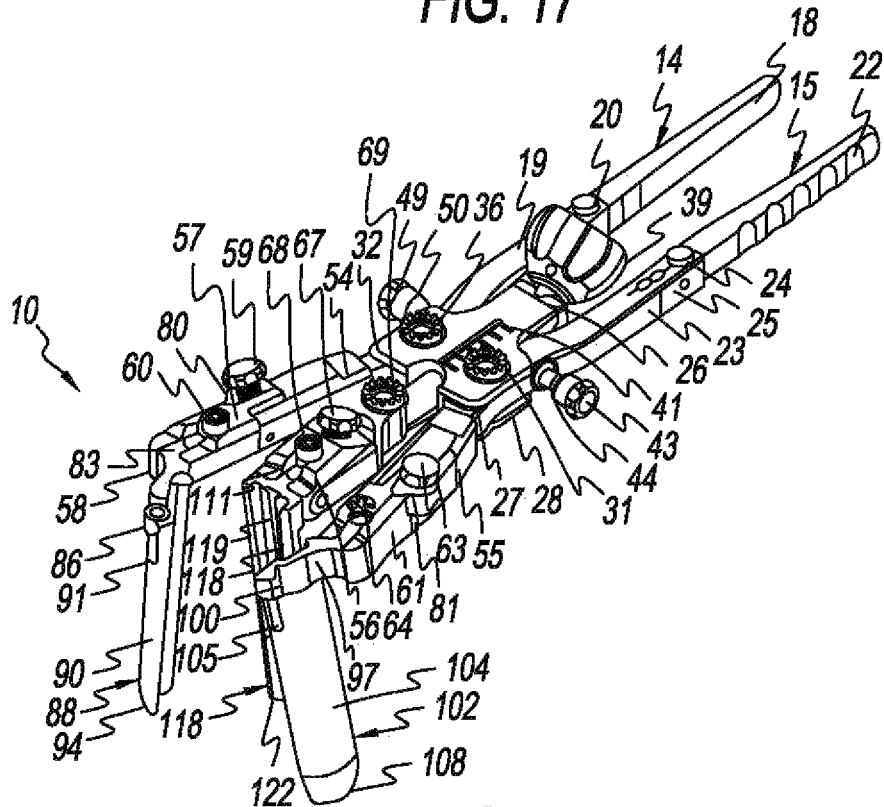
FIG. 18 is an isometric upper view of the orthopedic retractor of FIG. 1 shown with retractor blade and in a distracted state with an angulated lateral blade.

As best seen in FIGS. 20-24, as well as FIG. 7, the first lateral proximal arm 54 is connected at one end to the distal or lower end of the lower handle portion 19 of the first handle 14. The other end of the first lateral proximal arm 54 is pivotally connected to one end of the first lateral distal arm 57. The other end of the first lateral distal arm 57 terminates in an end 58 configured to receive a first lateral blade assembly 82 which holds the first lateral blade 88. The first lateral distal arm 57 pivots, angulates or tilts relative to the first lateral proximal arm 54 which, in turn, pivots, angulates or tilts the first lateral blade assembly 82 and thus the first lateral blade 88. In this manner, the first lateral blade 88 can angulate relative to the first lateral proximal arm 54 and thus the body 12. Angulation is controlled and adjusted by a first angulation assembly consisting of a first spherical pocket 74 in the first lateral proximal arm 54, a first spherical ball 75 situated in the first spherical pocket 74, and a first threaded angulation bolt 59 threadedly received in a first boss 80 of the first lateral proximal arm 54. The first angulation bolt 59 is received by the first spherical ball 75. Rotation of the first angulation bolt 59 produces or releases torque against the first spherical ball 75 which, in turn, causes the first lateral distal arm 57 to pivot in one direction or in an opposite direction, thereby providing controlled and adjustable angulation of the first blade holder assembly 82 and thus the first lateral blade 88 retained thereby.

The second lateral proximal arm 55 is connected at one end to the distal or lower end of the lower handle portion 23 of the second handle 15. The other end of the second lateral proximal arm 55 is pivotally connected to one end of the second lateral distal arm 61. The other end of the second lateral distal arm 61 terminates in an end 62 configured to receive a second lateral blade assembly 96 which holds the second lateral blade 102. The second lateral distal arm 61 pivots, angulates or tilts relative to the second lateral proximal arm 55 which, in turn, pivots, angulates or tilts the second lateral blade assembly 96 and thus the second lateral blade 102. In this manner, the second lateral blade 102 can angulate relative to the second lateral proximal arm 55 and thus the body 12. Angulation is controlled and adjusted by a second angulation assembly consisting of a second spherical pocket 76 in the second lateral proximal arm 55, a second spherical ball 77 situated in the second spherical pocket 76, and a second threaded angulation bolt 63 threadedly received in a second boss 81 of the second lateral proximal arm 55. The second angulation bolt 63 is received by the second spherical ball 77. Rotation of the first angulation bolt 63 produces or releases torque against the second spherical ball 77 which, in turn, causes the second lateral distal arm 61 to pivot in one direction or in an opposite direction, thereby providing controlled and adjustable angulation of the second blade holder assembly 96 and thus the second lateral blade 102 retained thereby.

The medial proximal arm 56 is connected at one end to a connection member 38 which in turn, is threadedly connected to the drive shaft 138 of the drive assembly 37. The drive assembly 37 controls medial distraction and retraction of the medial arm assembly and thus the medial blade 115 through rotation of the medial drive knob 39. The other end of the medial proximal arm 56 is pivotally connected to one end of the medial distal arm 65. The other end of the medial distal arm 65 terminates in an end 66 configured to receive a medial blade assembly 110 which holds the medial blade 115. The medial distal arm 65 pivots, angulates or tilts relative to the medial proximal arm 56 which, in turn, pivots, angulates or tilts the medial blade assembly 110 and thus the medial blade 115. In this manner, the medial blade 115 can angulate relative to the medial proximal arm 56 and thus the body 12. Angulation is controlled and adjusted by a medial angulation assembly consisting of a medial spherical pocket 78 in the medial proximal arm 56, a medial spherical ball 79 situated in the medial spherical pocket 78, and a medial angulation bolt 67 threadedly received in the medial proximal arm 56. The medial angulation bolt 67 is received by the medial spherical ball 79. Rotation of the medial angulation bolt 67 produces or releases torque against the medial spherical ball 79 which, in turn, causes the medial distal arm 65 to pivot in one direction or in an opposite direction, thereby providing controlled and adjustable angulation of the medial blade holder assembly 110 and thus the medial blade 115 retained thereby. Angulation of various of the blades is illustrated in FIGS. 17-20.

Figure 23:
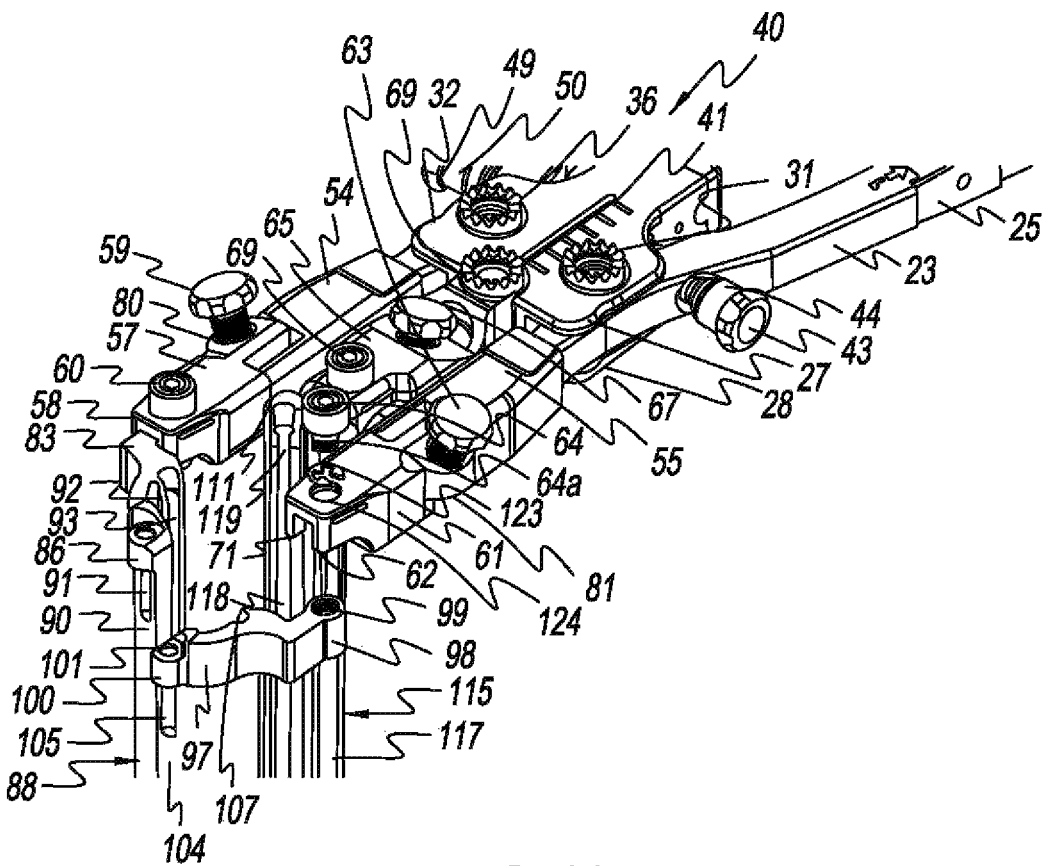
FIG. 23 is an enlarged isometric upper of the blade holder assembly of the orthopedic retractor of FIG. 1 illustrating how a blade assembly is received by the blade holder assembly.
Figure 24:
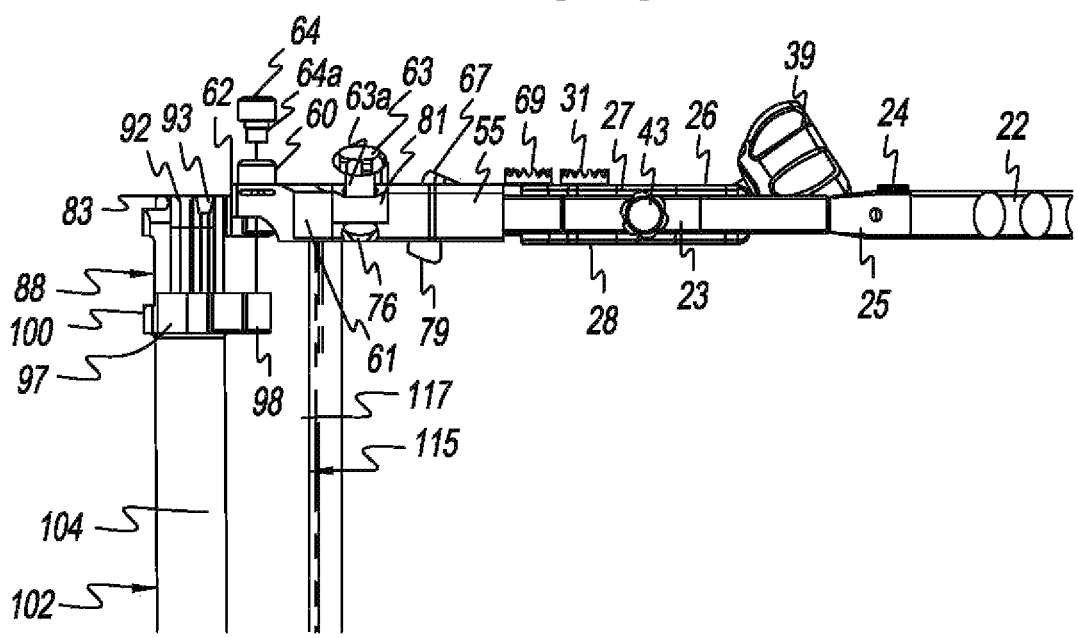
FIG. 24 is a side plan view of the orthopedic retractor depicted in FIG. 23.

As seen best in FIGS. 8-10 and 23-24, the first lateral blade holder assembly 82 includes a first lateral blade holder 83 and the first lateral blade 88 that extends from the first lateral blade holder 83. The first lateral blade holder 83 is configured as an elongated arm and includes a generally round boss 84 at one end having a threaded bore 85 extending therethrough, and a configured end 86 at another end opposite the boss 84 and having a bore 87 therethrough. The first lateral blade holder 83 is configured to be received in a like-configured notch 70 disposed in the underside of the distal end 58 of the first lateral distal arm 57. The threaded bore 85 receives a threaded shaft 60*a* of a first lateral blade lock bolt 60 extending through a bore 124 of the first lateral distal arm 57 in order to lock the first lateral blade holder 83 and thus the first lateral blade holder assembly 82 to the first lateral distal arm 57. As illustrated in FIG. 23, a c-clip 123 is provided to prevent the first lateral blade lock bolt 60 from coming out after the first lateral blade holder assembly 82 is removed.

The first lateral blade 88 is elongated and generally curved having a generally curved convex distal face 90 and a generally curved concave proximal face 89. The curved convex distal face 90 is generally smooth but having a slot 91 at its top axially beneath the bore 87. The bore 87 and slot 91 is configured to accept an instrument (not shown) that may aid in retraction. The curved concave proximal face 89 has various grooves or slots. Central dovetail configured slot 92 extending axially from the first lateral blade holder 83 to almost near a distal end 94 of the first lateral blade 88, accepts a light source cable (not shown) that can go down the dovetail to provide light into the disc space, or a blade extender (not shown) which may also interface with the other features. The dovetail slot 92 may include an interface 95 for connection purposes. Rounded slot 93 extends axially from the first lateral blade holder 83 to almost near the distal end 94. The rounded slot 93 accepts another light source cable (not shown) or other instrument (not shown).

The second lateral blade holder assembly 96 includes a second lateral blade holder 97 and the second lateral blade 102 that extends from the second lateral blade holder 97. The second lateral blade holder 97 is configured as an elongated arm and includes a generally round boss 98 at one end having a threaded bore 99 extending therethrough, and a configured end 100 at another end opposite the boss 99 and having a bore 101 therethrough. The second lateral blade holder 97 is configured to be received in a like-configured notch 71 disposed in the underside of the distal end 62 of the second lateral distal arm 61. The threaded bore 99 receives a threaded shaft 64*a* of a second lateral blade lock bolt 64 extending through a bore (not seen) of the second lateral distal arm 61 in order to lock the second lateral blade holder 97 and thus the second lateral blade holder assembly 96 to the second lateral distal arm 61. A c-clip (not seen) is provided to prevent the second lateral blade lock bolt 64 from coming out after the second lateral blade holder assembly 96 is removed.

The second lateral blade 102 is elongated and generally curved having a generally curved convex distal face 104 and a generally curved concave proximal face 103. The curved convex distal face 104 is generally smooth but having a slot 105 at its top axially beneath the bore 101. The bore 101 and slot 105 is configured to accept an instrument (not shown) that may aid in retraction. The curved concave proximal face 103 has various grooves or slots. Central dovetail configured slot 106 extending axially from the second lateral blade holder 97 to almost near a distal end 108 of the second lateral blade 102, accepts a light source cable (not shown) that can go down the dovetail to provide light into the disc space, or a blade extender (not shown) which may also interface with the other features. The dovetail slot 106 may include an interface (not seen) for connection purposes. Rounded slot 107 extends axially from the second lateral blade holder 97 to almost near the distal end 108. The rounded slot 107 accepts another light source cable (not shown) or other instrument (not shown).

Figure 20:
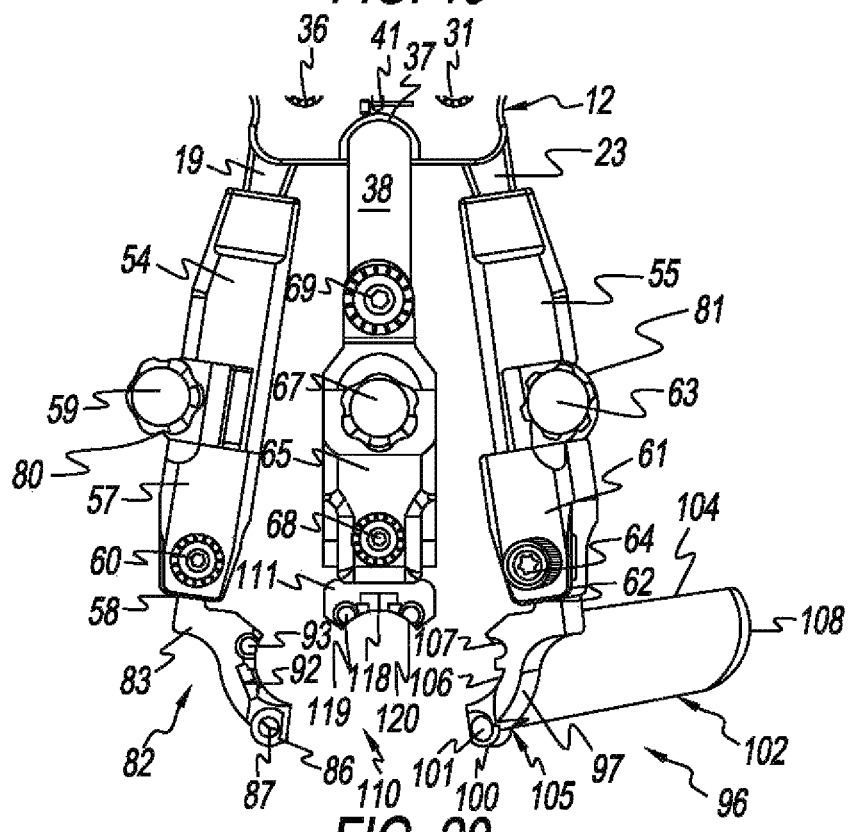
FIG. 20 is an enlarged top plan view of the blade holder assembly of the orthopedic retractor as depicted in FIG. 18.
Figure 21:
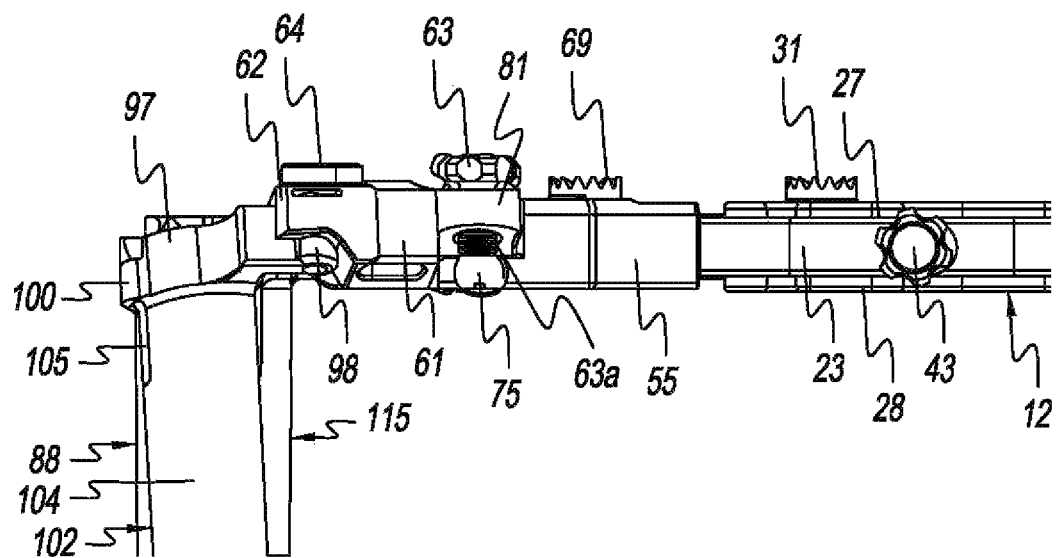
FIG. 21 is an enlarged side view of a portion of the blade holder assembly of the orthopedic retractor as depicted in FIG. 18.
Figure 22:
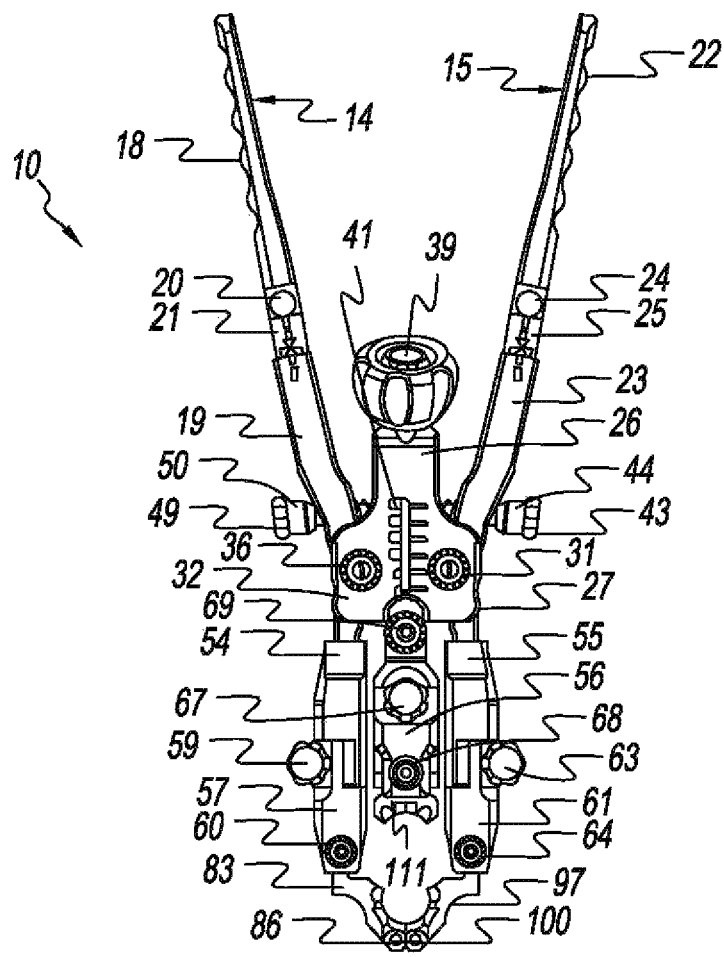
FIG. 22 is a top plan view of the orthopedic retractor of FIG. 1.

As seen in FIG. 20, the medial blade holder assembly 110 includes a medial blade holder 111 and the medial blade 115 that extends from the medial blade holder 111. The medial blade holder 111 is configured as an elongated arm and includes a generally round boss 113 in the middle of the medial blade holder 111 having a threaded bore 114 extending therethrough. The medial blade holder 111 is configured to be received in a like-configured notch 72 disposed in the underside of the distal end 66 of the medial distal arm 65. The threaded bore 114 receives a threaded shaft 68a of a medial blade lock bolt 68 extending through a bore (not seen) of the medial distal arm 65 in order to lock the medial blade holder 97 and thus the medial blade holder assembly 96 to the medial distal arm 65. A c-clip (not seen) is provided to prevent the medial blade lock bolt 68 from coming out after the medial blade holder assembly 96 is removed.

Figure 19:
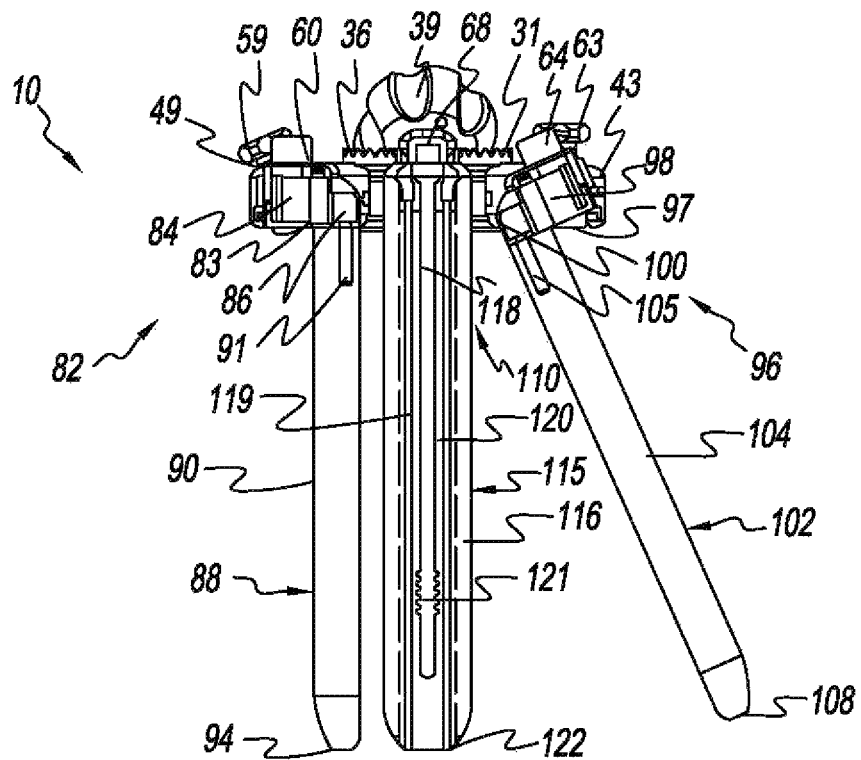
FIG. 19 is a front plan view of the orthopedic retractor as depicted in FIG. 18.

As seen in FIGS. 19 and 20, the medial blade is elongated and generally curved having a generally curved convex proximal face 117 and a generally curved concave distal face 116. The curved convex proximal face 117 is generally smooth. The curved concave distal face 116 has various grooves or slots. Central dovetail configured slot 118 extending axially from the medial blade holder 111 to almost near a distal end 122 of the medial blade 115, accepts a light source cable (not shown) that can go down the dovetail to provide light into the disc space, or a blade extender (not shown) which may also interface with the other features. The dovetail slot 118 may include an interface 121 for connection purposes. A first rounded medial slot 119 is disposed at one lateral side of the concave distal face 116 and extends axially from the medial blade holder 111 to almost near the distal end 122. A second rounded medial slot 120 is disposed at the other lateral side of the concave distal face 116 and extends axially from the medial blade holder 111 to almost near the distal end 122. The rounded slots 113, 120 accepts light source cables (not shown) or other instruments (not shown).

The present retractor 10 may be used for surgery other than procedures relating to the spine. Variations such as component size are contemplated as well as other manners or mechanisms for the features of the retractor presented herein.

It should furthermore be appreciated that dimensions of the components, structures, assemblies, and/or features of the present orthopedic retractor may be altered as desired within the scope of the present disclosure.

What is claimed is:

1. A medical retractor for lateral spine surgical procedures comprising:
   a body having a first lateral side a second lateral side;
   a first handle having a first distal handle portion pivotally attached to the body at the first lateral side, and a first proximal handle portion detachably coupled to the first distal handle portion;
   a first attachment and detachment assembly disposed between the first distal handle portion of the first handle and the first proximal handle portion of the first handle, the first attachment and detachment assembly having a first button configured to allow detachment of the first proximal handle portion of the first handle from the first distal handle portion of the first handle by pressing the first button, and to allow attachment of the first proximal handle portion of the first handle to the first distal handle portion of the first handle by pressing then releasing the first button;
   a first lateral arm assembly attached to the first handle;
   a first lateral blade attached to the first lateral arm assembly, the first handle controlling distraction of the first lateral blade relative to the body through movement of the first lateral arm assembly caused by pivotal motion of the first handle;
   a first distraction control assembly associated with the first handle and the body, and configured to adjust a pivotal position of the first handle to adjust distraction of the first blade;
   a first angulation assembly associated with the first lateral arm assembly and configured to adjust an angular orientation of the first lateral blade through angulation of the first lateral arm assembly;
   a second handle having a second distal handle portion pivotally attached to the body at the second lateral side, and a second proximal handle portion detachably coupled to the second distal handle portion;
   a second attachment and detachment assembly disposed between the second distal handle portion of the second handle and the second proximal handle portion of the second handle, the second attachment and detachment assembly having a second button configured to allow detachment of the second proximal handle portion of the second handle from the second distal handle portion of the second handle by pressing the second button, and to allow attachment of the second proximal handle portion of the second handle to the second distal handle portion of the second handle by pressing then releasing the second button;
   a second lateral arm assembly attached to the second handle;
   a second lateral blade attached to the second lateral arm assembly, the second handle controlling distraction of the second lateral blade relative to the body through movement of the second lateral arm assembly caused by pivotal motion of the second handle;
   a second distraction control assembly associated with the second handle and the body, and configured to adjust a pivotal position of the second handle to adjust distraction of the second blade;
   a second angulation assembly associated with the second lateral arm assembly and configured to adjust an angular orientation of the second lateral blade through angulation of the second lateral arm assembly;
   a medial drive assembly retained by the body, the medial drive including a threaded screw, wherein a portion of the threaded screw is exposed via a slot in the body;
   a medial arm assembly attached to the medial drive assembly;
   a medial blade attached to the medial arm assembly, the medial drive assembly controlling distraction of the medial blade relative to the body through movement of the medial arm assembly, wherein rotation of the threaded screw causes a change in distraction of the medial blade; and a medial angulation assembly associated with the medial arm assembly, and configured to adjust an angular orientation of the medial blade through angulation of the medial arm assembly.

2. The medical retractor for lateral spine surgical procedures of claim 1, wherein:

the first distal handle portion has a first distal handle portion proximal end and a first distal handle portion first distal end;

the second distal handle portion has a second distal handle portion second proximal end and a second distal handle portion second distal end;

the first lateral arm assembly has a first lateral proximal arm having a first lateral proximal arm first end and a first lateral proximal arm second end with the first lateral proximal arm first end connected to the first distal handle portion first distal end of the first distal handle portion, and a first lateral distal arm having a first lateral distal arm first end and a first lateral distal arm second end with the first lateral distal arm first end pivotally connected to the first lateral proximal arm second end, the first lateral blade attached to the first lateral distal arm second end;

the second lateral arm assembly has a second lateral proximal arm having a second lateral proximal arm first end and a second lateral proximal arm second end with the second lateral proximal arm first end connected to the second distal handle portion second distal end of the second distal handle portion, and a second lateral distal arm having a second lateral distal arm first end and a second lateral distal arm second end with the second lateral distal arm first end pivotally connected to the second lateral proximal arm second end, the second lateral blade attached to the second lateral distal arm second end; and the medial arm assembly has a medial proximal arm having a medial proximal arm first end and a medial proximal arm second end with the medial proximal arm first end connected to the medial drive assembly, and a medial distal arm having a medial distal arm first end and a medial distal arm second end with the medial distal arm first end pivotally connected to the medial proximal arm second end, the medial blade attached to the medial distal arm second end.

3. The medical retractor for lateral spine surgical procedures of claim 2, wherein:

the first angulation assembly comprises a first spherical pocket in the first lateral proximal arm, a first spherical ball situated in the first spherical pocket, and a threaded first knob situated in the first lateral distal arm, the threaded first knob in contact with the first spherical ball whereby torque applied to the first spherical ball by manipulation of the threaded first knob pivots the first lateral distal arm relative to the first lateral proximal arm to vary the angular orientation of the first blade;

the second angulation assembly comprises a second spherical pocket in the second lateral proximal arm, a second spherical ball situated in the second spherical pocket, and a threaded second knob situated in the second lateral distal arm, the threaded second knob in contact with the second spherical ball whereby torque applied to the second spherical ball by manipulation of the threaded second knob pivots the second lateral distal arm relative to the second lateral proximal arm to vary the angular orientation of the second blade; and the medial angulation assembly comprises a medial spherical pocket in the medial proximal arm, a medial spherical ball situated in the medial spherical pocket, and a threaded medial knob situated in the medial distal arm, the threaded medial knob in contact with the medial spherical ball whereby torque applied to the medial spherical ball by manipulation of the threaded medial knob pivots the medial distal arm relative to the medial proximal arm to vary the angular orientation of the medial blade.

4. The medical retractor for lateral spine surgical procedures of claim 3, wherein:

the first spherical pocket is disposed in the first lateral proximal arm second end;

the second spherical pocket is disposed in the second lateral proximal arm second end; and the medial spherical pocket is disposed in the medial proximal arm second end.

5. The medical retractor for lateral spine surgical procedures of claim 3, further comprising:

a first lateral blade holder configured to retain the first lateral blade and be received at and by the first lateral distal arm second end of the first lateral distal arm;

a second lateral blade holder configured to retain the second lateral blade and be received at and by the second lateral distal arm second end of the second lateral distal arm; and a medial blade holder configured to retain the medial blade and be received at and by the medial distal arm second end of the medial distal arm.

6. The medical retractor for lateral spine surgical procedures of claim 5, wherein:

the first lateral blade holder is configured to detachably retain the first lateral blade and be received at and by the first lateral distal arm second end of the first lateral distal arm;

the second lateral blade holder is configured to detachably retain the second lateral blade and be received at and by the second lateral distal arm second end of the second lateral distal arm; and the medial blade holder is configured to detachably retain the medial blade and be received at and by the medial distal arm second end of the medial distal arm.

7. The medical retractor for lateral spine surgical procedures of claim 5, wherein:

the first lateral distal arm second end of the first lateral distal arm includes a first lateral notch configured to receive the first lateral blade holder;

the second lateral distal arm second end of the second lateral distal arm includes a second lateral notch configured to receive the second lateral blade holder; and the medial distal arm second end of the medial distal arm includes a medial notch configured to receive the medial blade holder.

8. The medical retractor for lateral spine surgical procedures of claim 7, wherein:

the first lateral notch is configured to detachably receive the first lateral blade holder;

the second lateral notch is configured to detachably receive the second lateral blade holder; and the medial notch is configured to detachably receive the medial blade holder.

9. The medical retractor for lateral spine surgical procedures of claim 8, wherein:

the first lateral blade holder includes a first threaded blade holder bore;

the first lateral distal arm second end of the first lateral distal arm further includes a first threaded bore and a first threaded bolt disposed in the first threaded bore, the first threaded bolt configured for threaded reception in the first threaded blade holder bore of the first lateral blade holder to detachably retain the first lateral blade holder;

the second lateral blade holder includes a second threaded blade holder bore;

the second lateral distal arm second end of the second lateral distal arm further includes a second threaded bore and a second threaded bolt disposed in the second threaded bore, the second threaded bolt configured for threaded reception in the second threaded blade holder bore of the second lateral blade holder to detachably retain the second lateral blade holder;

the medial blade holder includes a medial threaded blade holder bore; and the medial distal arm second end of the medial distal arm further includes a medial threaded bore and a medial threaded bolt disposed in the medial threaded bore, the medial threaded bolt configured for threaded reception in the medial threaded blade holder bore of the medial blade holder to detachably retain the medial blade holder.

10. The medical retractor for lateral spine surgical procedures of claim 3, wherein the medial drive assembly comprises:

a drive knob rotatable in a first direction and in a second direction opposite the first direction; and a threaded shaft retained in the body and having a first shaft end and a second shaft end, the drive knob connected to the first shaft end, and the medial proximal arm connected to the second shaft end;

wherein rotation of the drive knob in the first direction distracts the medial blade, and rotation of the drive knob in the second direction retracts the medial blade.

11. The medical retractor for lateral spine surgical procedures of claim 10, further comprising a gauge disposed in the body and operably connected to the threaded shaft to indicate a distraction position of the medial blade.

12. The medical retractor for lateral spine surgical procedures of claim 1, wherein:

the first distraction control assembly comprises a first lateral knob having a first threaded knob shaft that is threadedly received through the first handle and into the body, and a first spring disposed on the first threaded knob shaft between the body and the first handle; and the second distraction control assembly comprises a second lateral knob having a second threaded knob shaft that is threadedly received through the second handle and into the body, and a second spring disposed on the second threaded knob shaft between the body and the second handle.

13. The medial retractor for lateral spine surgical procedures of claim 1, wherein the threaded screw includes a marker that is exposed via the slot in the body.

14. The medial tractor for lateral spine surgical procedures of claim 13, wherein the body further includes a gauge proximate the slot in the body, wherein the position of the marker relative to the gauge provides an indication of the amount of distraction of the medial blade.

15. The medial tractor for lateral spine surgical procedures of claim 1, wherein the body further includes a gauge proximate the slot in the body.

* * * * *